United States Patent [19]
Fujita et al.

[11] Patent Number: 5,789,252
[45] Date of Patent: Aug. 4, 1998

[54] METHOD OF WASHING CONTAINER USED FOR REACTION OF BODY LIQUID SAMPLE AND REAGENT

[75] Inventors: Hiroko Fujita, Takahagi; Mitsuo Hattori, Hitachinaka; Emi Murakami, Kashiwa; Yasuhisa Shibata, Oomiya-machi, all of Japan

[73] Assignees: Hitachi, Ltd., Tokyo; Hitachi Instruments Engineering Co., Ltd., Ibaraki, both of Japan

[21] Appl. No.: 731,674

[22] Filed: Oct. 17, 1996

[30] Foreign Application Priority Data

Oct. 18, 1995 [JP] Japan ..................... 7-269958

[51] Int. Cl.$^6$ .............. G01N 1/34; G01N 35/02; G01N 21/15; C11D 1/825
[52] U.S. Cl. .............. 436/49; 436/54; 436/180; 510/161; 510/179; 510/421; 510/422; 510/475; 510/499; 510/506; 134/22.14; 134/22.19; 422/63; 422/64
[58] Field of Search .................. 436/49, 43, 54, 436/180; 134/22.14, 22.19; 510/161, 179, 421, 422, 475, 499, 506; 422/63, 64

[56] References Cited

U.S. PATENT DOCUMENTS 3,856,711  12/1974  Mausner et al. ............... 252/545
4,878,951  11/1989  Pochard et al. ............... 134/22.17
5,109,127  4/1992   Sekiguchi et al. ............ 536/115
5,312,561  5/1994   Hoshino et al. ............. 252/174.12
5,441,667  8/1995   Tonomura et al. ............ 252/174
5,612,305  3/1997   Lewis ...................... 510/490

FOREIGN PATENT DOCUMENTS

5-164762  6/1993  Japan.

*Primary Examiner*—Long V. Le
*Attorney, Agent, or Firm*—Fay, Sharpe, Beall, Fagan, Minnich & McKee

[57] ABSTRACT

A body fluid sample and a reagent are reacted in a reaction container, and after measuring the reaction solution the reaction solution is discharged from the reaction container. The vacant reaction container is washed by charging a detergent solution containing plural kinds of surface active agents through a nozzle of a washing mechanism. The detergent solution is a mixed solution containing polyoxyethylene alkyl ether, polyoxyethylene polyoxypropylene glycol ether, N-acyl amino acid salt and polyacrylic salt. By the washing method in accordance with the present invention, it is possible to eliminate bad effects due to incomplete washing of reaction containers in an apparatus for automatically successively analyzing biological samples.

9 Claims, 3 Drawing Sheets

METHOD OF WASHING CONTAINER USED FOR REACTION OF BODY LIQUID SAMPLE AND REAGENT

BACKGROUND OF THE INVENTION

The present invention relates to a method of washing a container, and more particularly to a method of washing a container used for reaction of a body liquid sample and a reagent.

Automatic analyzers are used in most clinico-chemical assays which analyze biochemical components in a bionic sample, such as inorganic ions, proteins, nitrogen-containing components, sugars, fats, enzymes, hormones, drugs and so on in a blood or urine sample. In most of the automatic analyzers, except for analyzers using disposable reaction cuvettes, reaction cuvettes or reaction containers are washed after analyzing and are reused.

In recent years, it has often been observed that blood and urine contain proteins or fats, and some reagents contain protein components such as enzymes. Thereby, the reaction containers are apt to be attached with stains.

In order to cope with the stains, reaction containers have been washed with water in every test. In a specially improved apparatus, reaction containers have been automatically washed using a detergent. There are some products which have a washing mechanism for reaction containers as a maintenance function separately from the automatic washing mechanism.

Japanese Patent Application Laid-Open No.5-164762 discloses a method in which water is filled in a reaction container after analysis of a sample, the absorption spectrum of the reaction container filled with water is measured using a multi-wavelength photometer, and the cause of a stain of the reaction container is determined based on the spectral pattern. In the method of Japanese Patent Application Laid-Open No.5-164762, a detergent suitable for removing the stain is determined and the reaction container is washed using the selected detergent. Kinds of detergents disclosed in Japanese Patent Application Laid-Open No.5-164762 are acidic detergents, alkaline detergents and protein-decomposing enzyme containing detergents.

Known detergents can be classified as alkaline solutions, acid solutions, neutral detergents (surface-active agents), and hypochlorite agents.

The alkaline solutions such as sodium hydroxide have strong degreasing detergency and are effective for washing stains of proteins, organic substances, and oils and fats which are dissolved and decomposed. Further, the alkaline solutions are effective to suppress reproduction of microorganisms.

The neutral detergents emulsify stains, and dissolve and decompose the stains, and are effective for inorganic substances and organic substances.

The inorganic acids such as sulfuric acid, hydrochloric acid and the like show important detergency in the field of industrial washing, but they often have strong chemical action or strong toxicity. Therefore, in general, the component of the acid detergent used is an organic acid such as tartaric acid, citric acid or the like which has a low acidity and a low toxicity. The hypochlorite agent dissolves and decomposes stains. Further, the hypochlorite agents have effects to oxidize stains and flake and dissolve solidified stains by foaming. Furthermore, the hypochlorite agents are highly effective to suppress reproduction of microorganisms, and effective for organic substances, inorganic substances and sterilization of microorganisms.

As described above, each of the components of detergents is effective depending on the kind of stains, but the kinds of stains are not the same and degree of the stains is not the same since blood or urine contains proteins, fats and various other components, and pigments are contained in the measurement reagents.

Of course, it is preferable that the kind of detergent is selected depending on the kind and the degree of stains. However, in the case of an automatic analyzer, and particularly in a case of an automatic analyzer of a random access type for multi-item analysis with a single line, reaction solutions having various characteristics are injected into one reaction container. Therefore, it is difficult to perform automatic washing by selecting a detergent solution suitable for the stain during continuous analyzing. For this reason, in most automatic analyzers, washing is actually performed using only water or using only a single component of a detergent solution during continuous analyzing.

However, it is impossible to completely remove stains attached by each analysis using only the surface active agent solely or only the alkaline agent solely. As a result, it is required that accumulated and solidified stains are periodically removed using a detergent such as sodium hypochlorite or an enzymatic detergent by hand or by a mechanism specifically designed for washing. This causes a problem of making the maintenance complex. Further, the hypochlorite solutions are comparatively effective for various kinds of stains, but it is difficult to maintain an effective concentration because hypochlorite ions are easily decomposed by light and temperature. Furthermore, since the hypochlorite solutions are strong oxidizers, the hypochlorite solutions interfere with reactions and greatly affect analysis data when not completely removed. Therefore, the hypochlorite solutions cannot be used for automatic washing during continuous analysis.

In recent years, the regulation for environmental drainage including drain from hospitals and laboratories has become more severe environmental problems are being taken seriously. Thus, it is necessary to take the drainage of the automatic analyzer into consideration.

In general, waste liquid is required to be properly treated according to water pollution control laws, sewage water control laws and waste disposal control laws so as to not become sources of pollution and infection. Especially, waste liquids from automatic analyzers are required to be disinfected and sterilized since most of the waste liquids are patient examination samples. However, the most important problem is pH control. That is, recent automatic analyzers generally use an alkaline solution and an acid solution as the detergents as described above, and it is, necessary to take the pH of the waste liquid into consideration. The pH control value according to the control laws is within 5.8 to 8.6. When a detergent solution containing, for example, 0.1N— NaOH (pH is nearly 13) is used, it can be calculated that the thin waste water (including washing water and rinsing water used for various portions of the analyzer) contains alkali of 0.1 to 1.0 m mol/liter on a sodium hydroxide base. When actually a pH of a thin waste water is measured, the pH of the thin waste water is 10 to 11 which exceeds the control value.

A facility or a workshop performing chemical analysis or having analyzers usually has neutralization equipment for experimental waste water disposal. As for the automatic analyzer, in a facility not having any waste water treating equipment, such as a small scale hospital or a health examination center, a neutralization tank specifically used for waste water from the automatic analyzer is installed to perform neutralization treatment, or the waste liquid is temporarily stored in a waste water tank and drained after being neutralized by injecting chemicals by hand.

However, installation of a dedicated neutralization tank for each automatic analyzer is complex, and the required installation space is great. On the other hand, in a case of performing neutralization by hand, it is required to inject an acid or an alkali while the pH is being adjusted using a pH indicating agent. This is very hard and dangerous work.

Even in a case where a facility has neutralization equipment for treating waste water of the whole facility, there is a problem in that the maintenance management work of the neutralization equipment for the whole facility becomes enormous. Further, in addition to the problem of controlling pH of the waste water, a flow passage may be choked by an indissoluble salt which is formed by reaction between acid or alkali composing a detergent and a special component in a reagent for measurement.

In the automatic analyzer having a special function against stains as described above, other than the problem of pH there is a problem of affecting measured data when plural kinds of detergents are mixed in a reaction container or a reagent pipetting mechanism.

On the other hand, in the automatic analyzer, a reaction container is re-used for the next analysis by sucking and draining a reaction liquid inside the reaction container and washing the reaction container using a detergent, and then rinsing the reaction container in a short time. Therefore, in a case of using a surface active agent as the detergent of the automatic analyzer, speed of defoaming is a necessary condition. Sucking and draining of a sample, a reagent or a reaction liquid of the sample and the reagent, and sucking and draining of a waste liquid after washing using a detergent and rinsing water are performed by a sucking nozzle connected to a waste liquid bottle. The waste liquid bottle is connectedly to a vacuum pump to suck the waste liquid and drain it to a sewage pipe. When the foaming is large and hardly defoamed, the foam remains in the waste liquid bottle for a long time and flows in a vacuum tank to cause an error operation, or a sensor in a liquid collector inside the vacuum tank erroneously detects the foam as the waste liquid to cause an error operation of the apparatus or to stop the apparatus.

Further, in a case of using a surface active agent as a detergent, turbidity takes place depending on the concentration and may adversely affect the measurement. In addition to this, such turbidity is not preferable from the appearance as a commercial product.

SUMMARY OF THE INVENTION

An object of the present invention is to provide a washing method capable of effectively removing stains of a reaction container and capable of eliminating the pH treatment of the waste water after washing.

Another object of the present invention is to provide a washing method capable of preventing the erroneous operation of an analyzer caused by foaming due to washing.

A further object of the present invention is to provide a washing method capable of not producing turbidity in a reaction container at washing.

A further additional object of the present invention is to provide a washing method in which a flow passage in an automatic analyzing apparatus is prevented from being choked by reaction products produced on the basis of the reaction in the automatic analyzing apparatus of a component constituting a detergent with a certain component contained in a reagent for measurement.

The present invention is a washing method for a container used for reaction of a biological sample such as a body fluid and a reagent, and the method is characterized by comprising the steps of ejecting a reaction solution in the container from the container; injecting a mixed solution containing a surface active agent having foamability, a surface active agent suppressing foaming and a surface active agent for suppressing turbidness into the container from which the reaction solution is ejected; and ejecting the mixed solution in the container from the container.

It is preferable that the mixed solution further contains poly-acrylic acid salt. Sodium polyacrylate or potassium polyacrylate prevents stains detached from the wall surface of a container from re-attaching onto the wall surface of the container.

In a preferable embodiment of the present invention, poly-oxyethylene alkyl ether is used as the surface active agent having foamability; poly-oxyethylene poly-oxypropylene glycol ether is used as the surface active agent suppressing foaming; and N-acyl-amino acid salt is used as the surface active agent for suppressing turbidness. A practical poly-oxyethylene alkyl ether is expressed by a chemical formula $R-O-(CH_2CH_2O)_nH$ where R is an alkyl group having a carbon number from 8 to 20 and n is an integer of 3 to 12. N-acyl-amino acid salt is selected from sodium N-lauroyl sarcosinate, sodium N-lauroyl-N-methyl alaninate and potassium N-lauroyl sarcosinate.

DETAILED DESCRIPTION OF THE PREFERRED EMBODIMENTS

Before describing detailed embodiments, a description will be made of pieces of knowledge obtained from experiments conducted by the inventors of the present invention.

The inventors of the present invention found that by using a mixed solution combining plural kinds of surface active agents for washing a reaction container, stains attached on the inner surface of the reaction container could be dissolved and decomposed. Further, it was found that by properly combining surface active agents, foaming at washing could be suppressed and the mixed solution of plural kinds of detergents was not turbid.

It has been found that stains can be dissolved, decomposed, and further emulsified, dispersed and solubilized by combining several kinds of surface active agents. Further, it has been found that the detergent becomes transparent by preparation of the combination.

It is preferable that the surface active agents do not affect measuring, and are excellent in emulsion, dispersion and solubilization of hard-dissolvable substance, and are excellent in heat resistance, acid resistance, alkali resistance and chemical resistance, and main detergents are preferably non-ionic group surface active agents.

Non-ionic group active agents do not cause ionization in water. That is, hydrophilic groups are non-dissociative such as —OH, —O—, —CONH$_2$ and so on. A sufficient hydrophilic property cannot be obtained by one hydrophilic group, but a strong hydrophilic property can be totally shown when there are many hydrophilic groups in one molecule of active agent.

Examples of the non-ionic group surface active agents are poly-oxyethylene alkyl ether which is high in solubility, foamability, permeability and detergency; poly-oxyethylene alkyl phenyl ether which is high in wettability, permeability, and detergency, and which also has an anti-static ability; poly-oxyethylene sorbitan fatty acid ester which is slightly poor in detergency; and poly-oxyethylene hydrogenated castor oil which has a solubilizing ability for fatty substance but is slightly poor in detergency.

The non-ionic group detergents have an advantage in that the detergency does not decrease in an acid solution or to an acid stain, and it has stability in hard water. Further, it is possible to expect a multiplicative effect by mixing with an anion group active agent or a cation group active agent.

As the main surface active agent, the inventors of the present invention select poly-oxyethylene alkyl ether which is high in solubilizing ability to hard-soluble substances, foamability, permeability and detergency. The relationship of HLB value described below is used for structure determination of poly-oxyethylene alkyl ether, and particularly for determination of the addition number of ethylene oxides.

That is, it is considered that various actions such as emulsion, dispersion, detergency, foaming are determined by balance of the hydrophilic property and the lyophilic property which the hydrophilic group and lypohilic group of a substance show at a boundary surface of two phases to each of the phases. The HLB value (the numerical expression of hydrophile-lypohile balance) may be called an emulsifiability coefficient of a surface active agent. When the HLB value is small, the lypohilic property is strong, and when the HLB value is large, the hydrophilic property is strong. A surface active agent has a solubilizing action when the HLB value is 15 to 18, it has a detergency action when the HLB value is 13 to 15, it has an emulsifying action when the HLB value is 8 to 18, and it has a wettability action when the HLB value is 7 to 9. Design of a surface active agent suitable for an object is determined by the required phenomenon and the balance of the hydrophilic group and lypohilic group of molecules of the surface active agent. The hydrophilic property can be freely varied by changing of an ethylene oxide group —(CH$_2$CH$_2$O)$_n$—. In a surface active agent used for a main detergent, there is a relationship that the HLB value becomes large as the addition number of ethylene oxides is increased. That is, as a result of studies, it has been found that when the addition number of ethylene oxides is 3 to 9 moles, the surface active agent has wettability, detergency and emulsifiability. When the addition number of ethylene oxides is 10 to 15 moles, the surface active agent has detergency and emulsifiability but the permeability is slightly decreased. When the addition number of ethylene oxides is 15 to 20 moles, the surface active agent has emulsifiability, dispersing ability and solubilizing ability. Further, when the surface active agent is formed into an aqueous solution, the surface active agent is dispersed translucent or transparent when the addition number of ethylene oxides is 10 to 13 moles, and the surface active agent is dispersed transparent when the addition number of ethylene oxides is 13 to 20 moles. From these results, it has been determined that the addition number of ethylene oxides is preferably 3 to 12 moles.

The carbon number of alkyl groups also relates to detergency. When the carbon number is small, the surface active agent becomes lypohilic. When the carbon number is large, the surface active agent becomes hydrophilic. Since the hydrophilic property becomes too strong when the carbon number is below 8 and, to the contrary, the lypohilic property becomes too strong when the carbon number is above 20, the balance is lost and the characteristic of the surface active agent is degraded. Most commonly available surface active agents have a carbon number of 8 to 20. From the above facts, the carbon number of the alkyl group is determined as 8 to 20.

In the automatic analyzer for analyzing body fluid samples, a reaction container is used as a reaction container of the next analysis for a new sample by sucking and draining a reaction solution inside the reaction container, washing the container using a detergent, and then rinsing the container in a short time. Therefore, fast defoaming is a necessary condition of the detergent used for the automatic analyzer. Further, since the reaction liquid and waste liquid after washing are sucked by a vacuum pump, foam may cause erroneous operation of the apparatus. It has been found that in order to suppress foaming inside an apparatus, it is effective to add a special kind of surface active agent to the main surface active agent.

Although it is often thought that the characteristic of foam adsorbing stains is the main function of detergency, there are many surface active agents having a comparatively poor foamability but a better detergency. It is true that foams adsorb particles of stains and thereby the detergency of a detergent solution is improved, but foams selectively adsorb solid fine particles of stains. In a case of performing washing in an automatic analyzer, the stains are in a form of liquid, and excessive foaming decreases the efficiency of analysis and causes an error operation of the apparatus. Even a surface active agent having a better foamability may be decreased in its formability by adding another surface active agent. In such a case, the another surface active agent serves as a defoaming agent. A surface active agent having an HLB value of 1.5 to 3 has a function of a defoaming agent. From a result of the inventors' study, it has been clarified that poly-oxyethylene poly-oxypropylene glycol ether is suitable for a surface active agent to suppress foaming using a non-ionic group poly-oxyethylene alkyl ether.

This surface active agent for suppressing foaming is an active agent of a high polymer having lypohilic group poly-oxypropylene of propylene oxide polymer as lypohilic groups, and additionally polymerized ethylene oxide as hydrophilic groups. The surface active agent has little detergency as a single component. Therefore, in the present invention, the object of the addition of the active agent is not in its detergency but in use of its function as a defoaming agent to the main surface active agent. Further, among products of poly-oxyethylene poly-oxypropylene glicol ether, there exists a flake-shaped solid product which is rare among non-ionic active agents. It is preferable to use a flake-shaped product because a high working efficiency in producing a detergent can be attained.

Addition of an adjuvant (auxiliary substance) will be described below. The adjuvant is an agent which does not have any detergency by itself, but reinforces the detergency of the detergent when it is mixed. For example, inorganic salt irrespective of neutrality or alkalinity serves to further reduce surface and interface tension of a detergent aqueous solution. Addition of inorganic salt affects micelle formability of a detergent, the adsorption of stains is improved, and the dispersing and holding ability for stains is increased by reducing a critical concentration of micelle formation or by supplying a charge to the micelles.

Poly-acrylic acid salt is effective for preventing re-attachment of stains. It is estimated that the added poly-acrylic acid salt is adsorbed on a stain detached surface to increase the negative (−) charge, and protect the surface from the stains in the detergent solution by repulsing the stains charged negative (−), or preventing the stains from re-attaching by forming a protective colloid of the stains. Examples of the poly-acrylic acid salts are sodium poly-acrylate and potassium polyacrylate.

An acid amido type anion surface active agent of N-acyl amino acid salt is further added as an adjuvant for a protein solubilizing agent. Assisting of foaming action, washing action, permeating action and emulsifying action can be expected. However, when N-acyl amino acid salt is added to a mixed solution of another component detergent, it has been found that there is an effect to suppress turbidness of the main non-ionic group surface active agent due to high concentration and makes the solution transparent. Examples of N-acyl amino acid salt are sodium N-lauroyl sarcosinate, sodium N-lauroyl-N-methyl alaninate, potassium N-lauroyl sarcosinate and so on.

Although concentration of a detergent containing the surface active agents and the adjuvant are not particularly limited, it is preferable that the actual concentration of the sum of the surface active agents and the adjuvant is 0.005% to 1%. In an apparatus where room to install the detergent is limited and the surface active agents and the adjuvant are automatically diluted with water in the apparatus be pipetted, the concentration in the detergent is 0.05 to 10%, for example, with 10 times dilution. The concentration of sodium polyacrylate is not particularly limited, but it is preferable that the amount of sodium polyacrylate is nearly the same as the amount of the surface active agent.

As described above, the washing liquid used for washing the reaction containers is composed so as to make up individual washing characteristics with one another without compensation. That is, mixing several kinds of surface active agents increases abilities to dissolve, decompose, emulsify and disperse stains, and produces a stronger detergency to protein stains and fatty stains in a reaction liquid compared to a washing liquid having a single component of surface active agent. Thereby, there is no need to unnecessarily increase the concentration of washing liquid, and there is no worry about the effect of the detergent on measured data. Further, mixing several kinds of surface active agents sometimes produces insoluble complex salt to lose its surface active ability. However, in the case of the components of the detergent used in the present invention, the problem is not fatal, and in fact foaming is suppressed and the solution is clarified.

Further, since washing can be performed using only a single detergent tank if the mixed solution is provided, there is no need to provide a space for setting several kinds of detergents and a mechanism for operating the several kinds of detergents. Furthermore, operating cost of the apparatus can be suppressed low. Still further, the rinsing efficiency is high defoaming is fast. Further, it is possible to eliminate effects to the vacuum bottle and the vacuum pump for sucking solution after washing and the other mechanisms.

Since the detergent employed in the present invention has sufficient detergency and attention is sufficiently paid to the of the detergent on measured data, it is possible to provide an automatic analyzer in which the detergent can be used as an automatic detergent solution during continuous analysis, a totally automated washing can be realized, and the maintenance can be simplified. The components of the detergent do not react with the component of an analysis reagent.

Inside an automatic analyzer, there are some positions at which the temperature rises due to heat generated by mechanisms in operation, such as heat from a motor, heat from a constant temperature bath, heat from a photometer and so on. Although there is a mechanism to eject the heat using a fan, there may exist some places of which temperature is raised as high as about 80° C. There are some kinds of surface active agents which cause separation or turn cloudy under a high temperature depending on their characteristics. In a case where there is such a worry, it is possible to independently provide several kinds of surface active agents composing the detergent in an apparatus, and to automatically mix them at the timing when the detergent is to be used. It is also possible to provide condensed solutions of the individual surface active agents and to dilute them at the timing when the detergent is to be used. This construction has an advantage in that only a small space is needed in the apparatus.

An embodiment employing the present invention will be described below.

Figure 1:
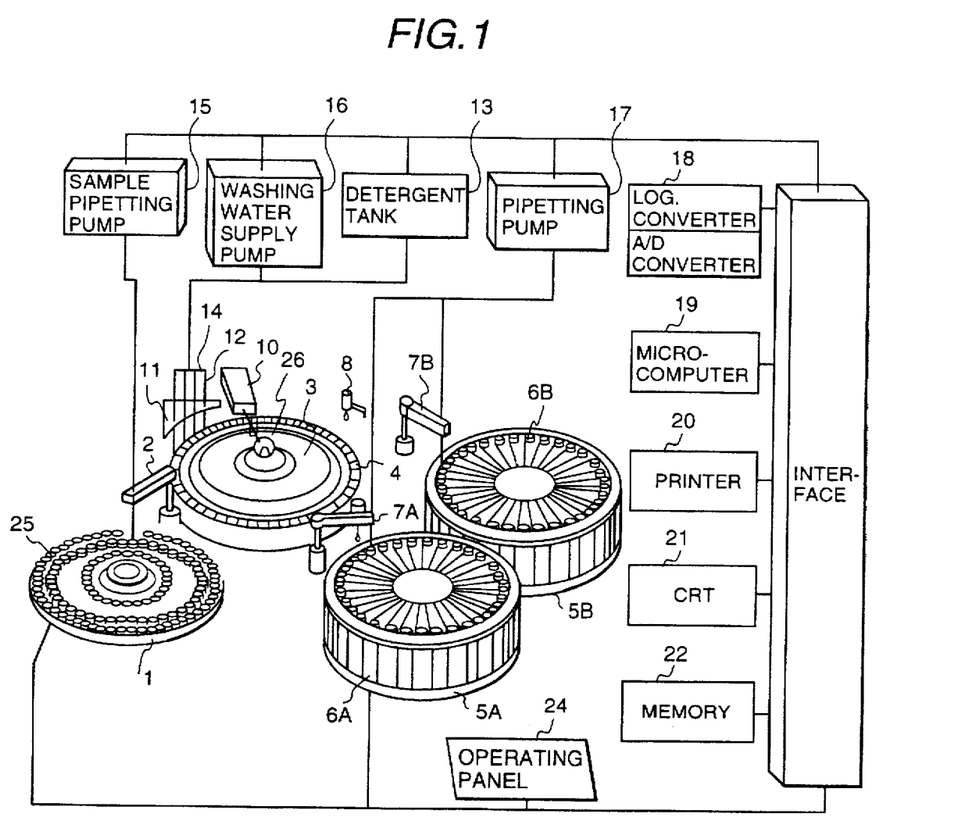
FIG. 1 is a sketch showing the construction of an automatic clinical analyzer for blood sample to which the present invention is applied.

FIG. 1 is a sketch showing the construction of an automatic analyzer for a body fluid sample. In FIG. 1, the reference character 3 indicates a reaction disk, and reaction containers (reaction containers or measurement cells) 4 (as many as, for example, 120 containers) are provided on the reaction disk 3. The whole of the reaction disk 3 is maintained at a given temperature by a constant temperature bath.

On a sample disk 1, there are arranged many sample containers 25 containing body fluid samples such as blood, serum, or urine. The samples in the sample containers 25 are delivered to reaction containers 4 on the reaction line using a sample delivery mechanism 2 having a pipette nozzle. On reagent disks 5A, 5B, there are provided many reagent vessels 6A, 6B for various analysis items. A pair of reagent delivery mechanisms 7A, 7B suck reagents corresponding to items to be analyzed in the pipette nozzles and discharge them to the reaction containers 4 on the reaction line. Around the reaction disk 3, there are arranged a stirring mechanism 8, a multi-wavelength photometer 10, a container washing mechanism 11 and so on. The array of the reaction containers 4 is moved by the reaction disk 3 so as to cross a light beam from a light source 26. The light beam passing though the reaction container is introduced to the photometer 10. The container washing mechanism 11 successively washes the reaction containers 4 containing the reaction solution having been measured.

The reference character 19 indicates a micro-computer, the reference character 23 indicates an interface, the reference character 18 indicates a Log converter and an A/D converter, the reference character 17 indicates a reagent pipetting pump, the reference character 16 indicates a washing water supply pump, and the reference character 15 indicates a sample pipetting pump. The reference character 20 indicates a printer, the reference character 21 indicates a CRT, the reference character 22 indicates a floppy disc as a memory, and the reference character 24 indicates an operating panel.

In the construction described above, an operator inputs analysis requesting information on each of the samples to be analyzed using the operating panel 24. The input analysis requesting information is stored in a memory in the micro-computer 19. A sample contained in a sample container 25 and set at a given position of the sample disk 1 is transferred into a reaction container 4 by a predetermined amount using the pipetting nozzle of the sample delivery mechanism 2 according to the analysis requesting information stored in the memory of the micro-computer 19.

The reaction disk 3 mounting the reaction containers 4 is rotated one turn plus one reaction container portion (i.e., through 121 containers if there are 120 containers on the disk) every machine cycle (20 seconds). A proper reagent vessel 6 is selected among the reagent vessels 6A, 6B arranged on the reagent disks 5A, 5B according to the analysis requesting information stored, and a given amount of the reagent is pipetted in the reaction container 4 having the delivered sample by the nozzles of the reagent delivery mechanisms 7A, 7B using the pipetting pump 17, and then stirred and mixed using a stirring mechanism 8. The reaction process of the sample and the reagents in the reaction container 4 is light-measured every certain period using the multi-wavelength photometer 10 to measure light absorption of the mixed solution using two preset wavelengths depending on each of the analysis items. The signal expressing the measured light absorption is input to the micro-computer 19 through the logarithmic converter, the A/D converter 18, and the interface 23.

The input light absorption signal is converted into a darkness value and the darkness value of each of the analysis items is stored in a floppy disc 22 and output to a printer 20. It is also possible to display the result of the examination data on a CRT 21.

The reaction container 4 after measurement is washed using the washing mechanism 11. That is, the reaction solution having been measured in the reaction container is first sucked by a sucking nozzle 12, and then a detergent 13 supplied from a tank 13 is injected into the vacant reaction container by an injection nozzle 14. Next, after discharging the detergent, distilled water pumped from a washing water supply pump 16 is injected into the reaction container and then sucked to be discharged. The injection and the sucking are repeated several times, and then water washing (water rinsing) is performed, and thus the washing is completed. The reaction container after washing is to be used for the next analysis on the reaction line.

Figure 2:
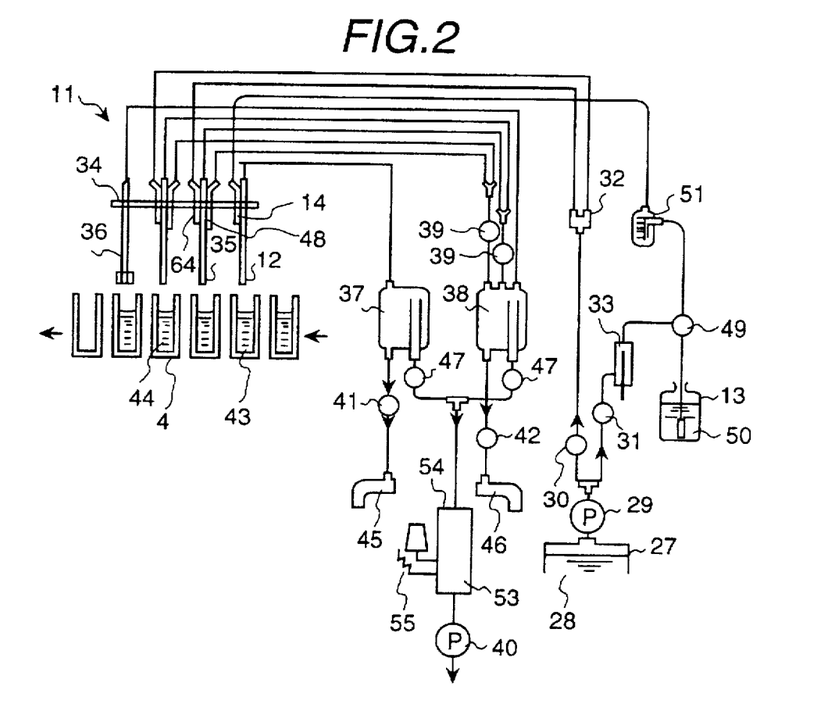
FIG. 2 is a diagram showing the flow paths of a container washing mechanism in the analyzer of FIG. 1.

FIG. 2 is a diagram showing the flow paths of a container washing mechanism in the analyzer of FIG. 1. In FIG. 2, washing water 28 in a distilled water tank 27 is supplied to a branch pipe 32 and a syringe 33 via water supply electromagnetic valves 30, 31 by a water supply pump 29. The washing water distributed by the branch pipe 32 is injected into a reaction container 4 through a water supply nozzle 64. On the other hand, as for a waste liquid system, a sucking nozzle 12 is connected to a dense waste liquid bottle 37, and a sucking nozzle 35 and a sucking nozzle 36 are connected to a thin waste liquid bottle 38 via sucking electromagnetic valves 39. The dense waste liquid bottle 37 and the thin waste liquid bottle 38 are connected to a vacuum tank 53 connected to a vacuum pump 40 and to waste liquid electromagnetic valves 41, 42.

Since the vacuum tank 53 is brought to a depressurized state by the vacuum pump 40, the dense waste liquid 43 in the reaction container 4 is sucked into the dense waste liquid bottle 37 through the sucking nozzle 12 and the thin waste liquid 44 is sucked into the thin waste liquid bottle 38 through the sucking nozzle 35. Then, the dense waste liquid and the thin waste liquid are exhausted to a sewage pipe 45 and a sewage pipe 46 through independent flow paths, respectively. The waste liquid sucked by the sucking nozzle 36 in the last stage is also sucked into the thin waste liquid bottle 38. During sucking a nozzle arm 34 is moved downward and the sucking electromagnetic valve 39 and the vacuum electromagnetic valve 47 are opened and the waste liquid electromagnetic valves are closed. By doing so, the waste liquid in the reaction container 4 is sucked. After that, the waste liquid is-exhausted through the inverse operation of the valves. Injection of washing water to the reaction container 4 is performed in synchronism with the waste liquid exhausting operation. In order to suck washing water over-flowed from the reaction container 4 in this time, an over-flow nozzle 48 is provided. The vacuum tank 53 has a vacuum detector 54 and a liquid collector detector 55. That is, when a small portion of the waste liquid to be exhausted from the dense waste liquid bottle 37 and the thin waste liquid bottle 38 to the sewage pipe 45 and the sewage pipe 46 flows and is collected in the vacuum tank 53, the liquid collector detector 55 operates to stop operation of the mechanism or to stop operation of the whole apparatus. However, when the present invention is not employed and accordingly foaming of the waste liquid after washing is excessively large and defoaming is slow, a large amount of foam remaining in the waste bottles 37, 38 gradually flows into the vacuum tank 53 and the liquid collector detector 55 erroneously operates to stop operation of the mechanism. Especially, in a case where the reaction containers are continuously washed or cell blank measurement of the reaction container is performed, the erroneous detection due to foam is apt to occur.

On the other hand, in a case where a detergent solution is supplied to the reaction container 4, a predetermined amount of detergent stock solution 50 is sucked in a syringe side by closing the water supply electromagnetic valve 31, turning the detergent electromagnetic valve 49 to the conducting flow path side of a detergent tank 13 containing the detergent stock solution 50 and the syringe 33, and moving the syringe 33 downward. Then, the syringe 33 is moved upward and at the same time the water supply electromagnetic valve 31 is opened. At this moment, by switching the detergent electromagnetic valve 49 to the conducting side of the flow path in a mixing bottle 51 side, the detergent stock solution sucked in the flow path is conducted into the mixing bottle 51 together with distilled water 28, and injected into the reaction container 4 by a detergent injecting nozzle 14 after being uniformed. By the operation described above, the reaction liquid and the washing waste water are exhausted outside the apparatus through the sewage pipe 45 and the sewage pipe 46.

Figure 3:
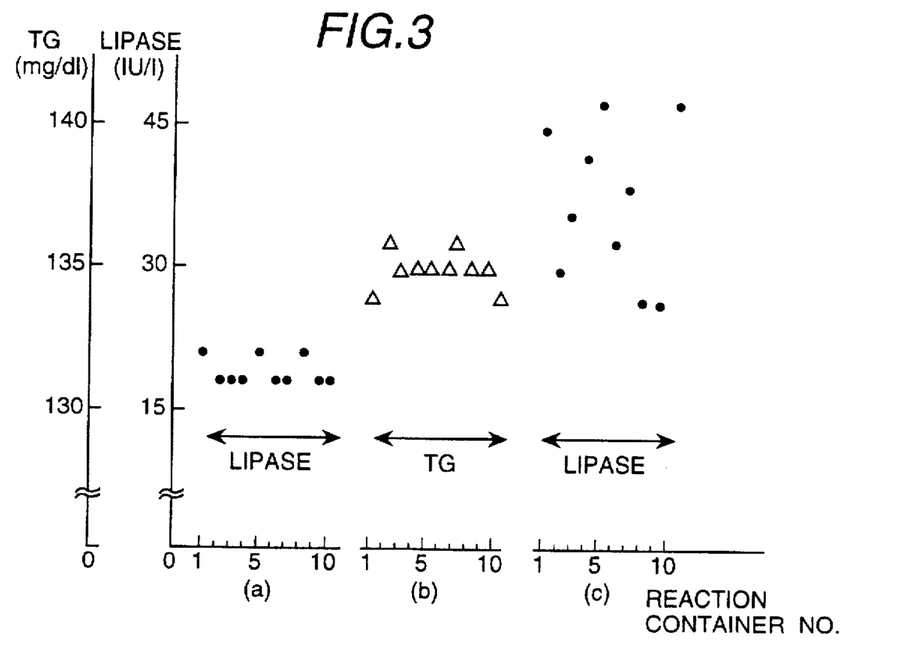
FIG. 3 is a graph showing measured results of neutral fat (TG) and lipase in a case of employing a conventional washing method.

FIG. 3 shows measured results of neutral fat (TG) and lipase as analysis items using a conventional single surface active active agent as a detergent for an automatic washing while continuously analyzing samples. The surface active agent used is 0.4% poly-oxyethylene (5) lauryl ether. In the state (a) of reaction container without stains, the average value of 10 lipase measurements is 18.2 IU/liter, and the reproduction deviation at single measurement is nearly 1.0 IU/liter. However, in a case (c) where lipase is measured using reaction containers that have been used for neutral fat (TG) measurement (b), the average value of lipase measurements is 31.4 IU/liter which is higher by 13.4 IU/liter and not measured correctly. Further, the deviation becomes large. This is because lipoprotein lipase contained in a reagent for measuring neutral fat (TG) is not washed completely and remains in the reaction container.

Figure 4:
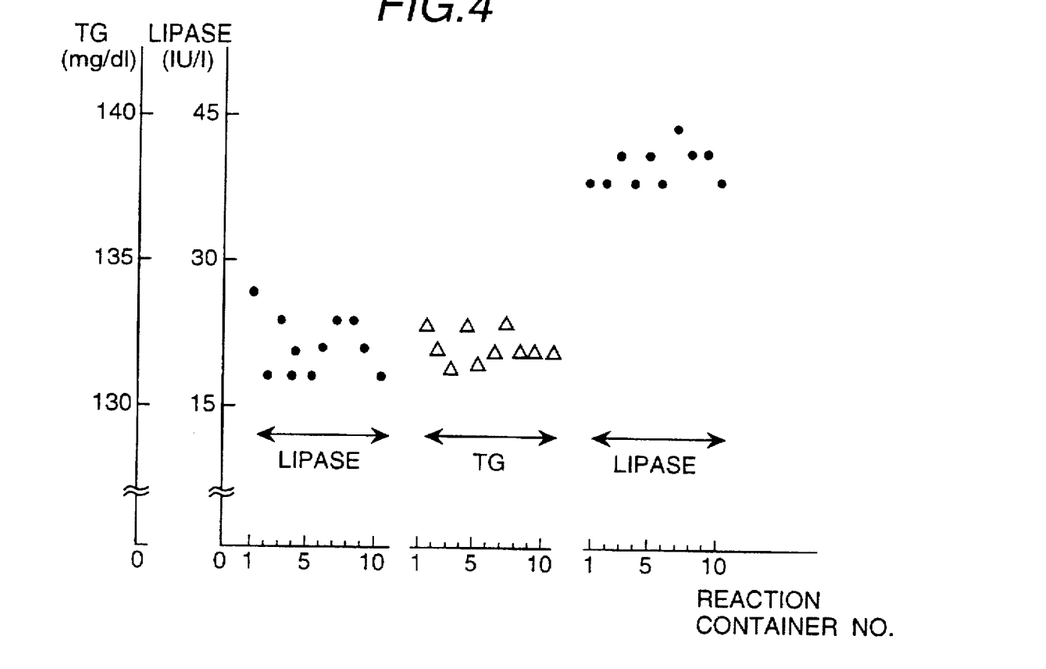
FIG. 4 is a graph showing measured results of neutral fat and lipase in a case where reaction containers are multi-stage washed using plural kinds of surface active agents.

FIG. 4 shows measured results obtained through multi-stage washing in which the reaction containers are once washed using one kind of surface active agent after measuring neutral fat (TG), and the reaction containers are washed using another kind of surface active agent, and furthermore washing the reaction containers using another kind of surface active agent, and then measuring lipase. The surface active agents used are 0.3% poly-oxyethylene (5) lauryl ether, 0.06% poly-oxyethylene poly-oxypropylene glycol ether, 0.03% sodium N-lauroyl sarcosinate and 0.2% sodium polyacrylate as another component. In the initial state of the reaction containers, the average value is 13.2 IU/liter, and in the case of re-using containers after multi-stage washing using several kinds of surface active agents, the average value is 28.5 IU/liter. The difference from the correct value is not improved at all compared to the data shown in FIG. 3. It can be understood that separately using of washing components cannot obtain a sufficient washing effect. Further, foaming in the first surface active agent is large, and measurement takes a long time because of low efficiency of rinsing the reaction containers.

Figure 5:
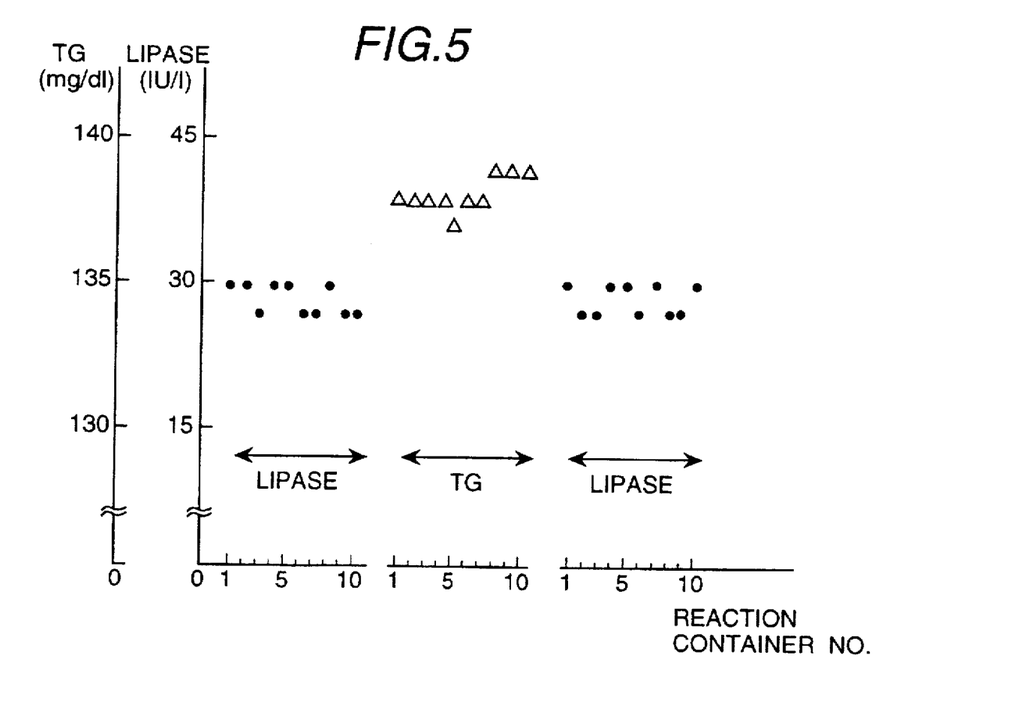
FIG. 5 is a graph showing measured results of neutral fat and lipase in a case where reaction containers are washed in accordance with the present invention.

FIG. 5 shows measured results of the same neutral fat (TG) and lipase measured as in FIG. 3 and FIG. 4 by the same analyzer using a washing solution having a mixture of plural kinds of surface active agents and an adjuvant according to the present invention as a detergent for automatic washing during continuous analyzing. The washing solution used in this embodiment is prepared by mixing 0.2% sodium polyacrylate to 0.25% poly-oxyethylene (5) lauryl ether, 0.05% poly-oxyethylene poly-oxypropylene glycol ether, and 0.03% sodium N-lauroyl N-methyl alaninate. In the state of reaction container without stains, the average value is 14.4 IU/liter. Even when lipase is measured using the reaction containers having been used for the precedent measurement of neutral fat (TG), the average value is 14.2 IU/liter which is correctly measured without effect of neutral fat (TG). Thus, the detergent effect of the detergent in accordance with the present invention can be confirmed.

The same detergent effect can be confirmed when sodium N-lauroyl sarcosinate is used instead of sodium N-lauroyl-N-methyl alaninate. Although mixing of 0.3% poly-oxyethylene (5) lauryl ether, 0.06% poly-oxyethylene poly-oxypropylene glycol ether and 0.2% sodium polyacrylate produces muddiness in a high concentration surface active agent, it is also confirmed that the muddiness can be turned transparent by further adding of 0.03% sodium N-lauroyl sarcosinate or 0.03% sodium N-lauroyl-N-methyl alaninate to the mixed solution.

Further, pH neutralization for the waste liquid exhausted after washing in FIG. 5 is not required because the washing does not use alkali and acid, and accordingly the related treatments and the operating cost are unnecessary. Further, danger and troublesomeness associated with neutralization treatment by hand are unnecessary.

In the case of the washing solution used in the present invention, foaming during washing is suppressed and foam does not remain in the waste liquid bottle, and accordingly erroneous operation of the apparatus does not take place at all.

Table 1(A) and Table 1(B) show comparison of foaming and defoaming in waste liquid bottles of automatic analyzers when detergents of various combinations of surface active agents are used.

TABLE 1 (A)

| No. | surface active agents by kind | a type automatic analyzer | | | | b type automatic analyzer | | | |
| --- | --- | --- | --- | --- | --- | --- | --- | --- | --- |
| | | cell blank | | routine measuring | | cell blank | | routine measuring | |
| | | F | D | F | D | F | D | F | D |
| A' | 5% non-ionic[1] + 1% ampho-ionic | x | x | ○ | △ | △ | △ | ○ | △ |
| C | 2.5% non-ionic[2] + 0.5% non-ionic[3] | ○ | ○ | ⊙ | ⊙ | ○ | ⊙ | ○ | ⊙ |
| C' | 5% non-ionic[2] + 1% non-ionic[3] | ○ | ○ | ⊙ | ⊙ | ⊙ | ⊙ | ⊙ | ⊙ |
| D | 2.5% non-ionic[1] + 0.5% non-ionic[3] | x | x | ○ | △ | △ | ○ | △ | ○ |
| A | 2.5% non-ionic[1] + 0.5% ampho-ionic | x | x | ○ | △ | △ | ○ | △ | ○ |
| D' | 5% non-ionic[1] + 1% non-ionic[3] | ○ | ○ | ⊙ | ○ | △ | ○ | ○ | △ |

Note:
F; foaming
D; defoaming

TABLE 1(B)

| | foaming | defoaming |
| --- | --- | --- |
| ⊙ | no bubbles formed | no bubbles remained |
| ○ | small bubbles formed | small bubbles remained |
| △ | middle size bubbles formed | middle size bubbles remained |
| x | large bubbles formed | large bubbles remained |

Detergent No. A to D in Table 1(A) indicate kind of detergent. The non-ionic surface active agent [1] in the table is poly-oxyethylene (9) alkyl ether, the non-ionic surface active agent [2] is poly-oxyethylene (5) lauryl ether which is a kind of poly-oxyethylene alkyl ether (the carbon number of R is 12), and the non-ionic surface active agent [3] is poly-oxyethylene poly oxypropylene ether. In the combination of [1] poly-oxyethylene (9) alkyl ether and [3] poly-oxyethylene poly-oxypropylene glycol ether, the combination is possible to be practically used because small bubbles spontaneously eliminate though it is a combination of non-ionic surface active agents. On the other hand, in the combination of [1] poly-oxyethylene (9) alkyl ether and ampho-ionic surface active agent, the combination is difficult to be practically used because large bubbles remain in the waste liquid bottle.

On the other hand, it is found that foaming is completely suppressed in a case of combination of [2] poly-oxyethylene (5) lauryl ether and [3] poly-oxyethylene poly oxypropylene glycol ether, which is used in the present invention. This difference is clearly shown in the cell blank measuring rather than in the routine measuring.

Since foaming and defoaming may possibly depend on mechanistic differences such as shape of waste liquid bottle and mechanism of sucking and the mechanism of ejection, the same study has been performed using several types of commercially available analyzers. As a result, it has been found that only the combination of surface active agents according to the present invention can suppress foaming.

Table 2(A), Table 2(B) and Table 2(C) show a comparison of washing effects using reaction containers made of different materials by using detergents of various combinations of surface active agents as automatic washing detergents during continuous analyzing.

TABLE 2 (A)

| cell material detergent combination | PMMA | | | | poly-methyl pentene | | | non-crystal poly-olefin | | |
|---|---|---|---|---|---|---|---|---|---|---|
| of carry-over | A | B | C | D | A | C | D | A | C | D |
| T-CHO → NEFA | x | x | Δ | x | O | O | Δ | Δ | O | O |
| TG → NEFA | x | x | Δ | x | O | O | x | O | Δ | Δ |
| T-CHO → F-CHO | x | x | Δ | x | O | O | O | x | O | Δ |
| TTT → TG | O | Δ | O | Δ | O | O | O | O | O | O |
| TG → F-CHO | x | x | Δ | x | O | O | O | O | O | O |

TABLE 2 (B)

| No. | surface active agents by kind |
|---|---|
| A | non-ionic[1] + ampho-ionic |
| B | non-ionic[1] + anionic |
| C | non-ionic[2] + non-ionic[3] |
| D | non-ionic[1] + non-ionic[3] |

TABLE 2 (C)

| | |
|---|---|
| O | excellent |
| Δ | no problem |
| x | problem existing |

Materials for the reaction containers used are PMMA (poly-methyl methacrylate), polymethyl pentene and non-crystal poly-olefin. Each of these materials has different properties and different characteristics, and is used for a reaction container.

Combination of carry-over in Table 2(A) means that the top item is an item influencing an effect when the same reaction container is used, and the tail item after an arrow is an item influenced by the effect. The detergent No. in Table 2(B) is the same as in Table 1. It has been confirmed that only the detergent C in Table 2(B) used in the present invention has a better washing effect for all the kinds of the reaction containers. Particularly, the effect is outstanding for poly-methyl pentene and noncrystal polyolefin.

Although the above description is made on examples in which the present invention is applied to washing of the reaction containers, the detergent solution of this kind can be applied to washing of the sample pipetting nozzle, the reagent pipetting nozzle, and the stirring rod of an automatic analyzer. These mechanisms may cause erroneous operations if there are insufficient washing, or remaining reagents or stains, the same as in the case of the reaction containers.

According to the detergent solution in accordance with the present invention, the detergent is excellent in solubilizing ability, decomposing ability, permeability, dispersing ability, emulsifiability of stains, and in capability of making hard-soluble substances soluble compared to the conventional detergents. Therefore, it is possible to successively analyze items affecting each other, which has been considered to be difficult to analyze. Therefore, it is possible to obtain accurate measured results for analysis items, to eliminate erroneous data due to insufficient washing, and to perform measurement without reducing analyzing speed. Further, since the washing can be completely automated, periodical maintenance troublesomeness can be eliminated. Since the detergent has a high washing effect, it is possible to reduce the running cost. Furthermore, the detergent of the present invention does not affect the measured data. In addition to these, since the detergent is less foaming and better defoaming, the detergent improves the washing efficiency and does not affect the hardware of the apparatus such as the vacuum mechanism.

Further, pH neutralization for the waste liquid after being exhausted is not required because the washing does not use alkali and acid, and accordingly the related treatments and the operating cost are unnecessary. Further, danger and troublesomeness associated with neutralization treatment by hand are unnecessary.

Further, the detergent itself is transparent, and accordingly there is no worry to affect measurement, and there is no problem as a commercial product.

Furthermore, since components in the detergent do react with components contained in a measuring reagent even if the detergent is mixed in the apparatus, there is no trouble in the hardware of the apparatus at all.

What is claimed is:

1. A method of washing a container in which a biological sample has reacted with a reagent to produce a reaction solution, comprising the steps of:
   (a) ejecting the reaction solution from the container;
   (b) after step (a), injecting a diluted dense detergent mixture containing poly-oxyethylene alkyl ether, poly-oxyethylene poly-oxypropylene glycol ether and poly-acrylic acid salt and a diluent into the container;
   (c) ejecting the diluted dense detergent mixture from the container; and
   (d) after step (c), washing the container with pure water.

2. A method according to claim 1, wherein said poly-acrylic acid salt is any one of sodium polyacrylate and potassium polyacrylate.

3. A method according to claim 1, wherein the diluted dense detergent mixture further contains N-acyl-amino acid salt.

4. A method of washing a container in which a biological sample has reacted with a reagent to produce a reaction solution, comprising the steps of:
   (a) ejecting the reaction solution from the container;
   (b) after step (a), washing the container with a mixed solution of surface active agents, without a step of washing said container with an acidic detergent and without a step of washing said container with an alkaline detergent, said mixed solution including poly-oxyethylene alkyl ether as a major component and poly-oxyethylene poly-oxypropylene glycol ether and poly-acrylic acid salt as other components;
   (c) ejecting the mixed solution from the reaction container; and
   (d) after step (c), washing the container with pure water.

5. A method according to claim 4, wherein said poly-oxyethylene alkyl ether is expressed by a chemical formula R—O—$(CH_2CH_2O)_n$H, where R is an alkyl group having a carbon number of 8 to 20 and n is an integer of 3 to 12.

6. A method according to claim 4, wherein said mixed solution further includes N-acyl-amino acid salt.

7. A method according to claim 6, wherein said N-acyl-amino acid salt is selected from the group consisting of sodium N-lauroyl sarcosinate, sodium N-lauroyl-N-methyl alaninate, and potassium N-lauroyl sarcosinate.

8. A method according to claim 4, wherein step (b) comprises the steps of mixing a dense detergent mixture and a diluent in a mixing bottle to thereby obtain said mixed solution; and discharging said mixed solution from said mixing bottle to said container through an injection nozzle.

9. An automatic analyzer in which a body fluid sample and a reagent are reacted with each other in a container to produce a reaction solution, the reaction solution is measured, and the container is washed, comprising:

a detergent solution bottle accommodating a dense detergent solution including a plurality of kinds of surface active agents, including poly-oxyethylene alkyl ether, poly-oxyethylene poly-oxypropylene glycol ether and poly-acrylic acid salt;

an injection nozzle;

a mixing bottle;

means for feeding the dense detergent solution to the mixing bottle;

means for feeding pure water as a diluent to the mixing bottle so as to dilute the dense detergent solution with the pure water;

means for feeding the diluted dense detergent solution through the injection nozzle to the container after the reacted solution has been ejected from the container;

a waste liquid bottle whose interior is depressurized; and a sucking nozzle through which the diluted dense detergent solution in the container is sucked towards the waste liquid bottle.

* * * * *